United States Patent
Beckmann et al.

(10) Patent No.: US 9,858,393 B2
(45) Date of Patent: Jan. 2, 2018

(54) SEMANTIC COMPRESSION

(75) Inventors: Nathan Beckmann, Cambridge, MA (US); Miodrag Potkonjak, Los Angeles, CA (US)

(73) Assignee: EMPIRE TECHNOLOGY DEVELOPMENT LLC, Wilmington, DE (US)

(*) Notice: Subject to any disclaimer, the term of this patent is extended or adjusted under 35 U.S.C. 154(b) by 533 days.

(21) Appl. No.: 12/997,862

(22) PCT Filed: Apr. 13, 2010

(86) PCT No.: PCT/US2010/030950
§ 371 (c)(1),
(2), (4) Date: Dec. 13, 2010

(87) PCT Pub. No.: WO2011/129816
PCT Pub. Date: Oct. 20, 2011

(65) Prior Publication Data
US 2012/0265738 A1     Oct. 18, 2012

(51) Int. Cl.
*G06F 17/30*     (2006.01)
*G06F 19/00*     (2011.01)
*H03M 7/30*     (2006.01)

(52) U.S. Cl.
CPC ............ *G06F 19/345* (2013.01); *H03M 7/30* (2013.01); *G06F 19/3443* (2013.01); *G06F 19/3493* (2013.01)

(58) Field of Classification Search
CPC .................................................... G06F 19/345
See application file for complete search history.

(56) References Cited

U.S. PATENT DOCUMENTS 4,202,340 A    5/1980   Langer et al.
5,146,228 A    9/1992   Irani et al.
(Continued)

FOREIGN PATENT DOCUMENTS

WO    WO-2011/129817    10/2011

OTHER PUBLICATIONS

"An intelligent system based on fuzzy probabilities for medical diagnosis—a study in aphasia diagnosis"; Moshtagh-Khorasani et. al; Mar.-Apr. 2009; Journal of Research in Medical Sciences; Edition. 14(2): p. 89-103. https://www.ncbi.nlm.nih.gov/pmc/articles/PMC3129094/.*

(Continued)

*Primary Examiner* — Elaine Gort
*Assistant Examiner* — Rajiv Raj
(74) *Attorney, Agent, or Firm* — Brundidge & Stanger, P.C.

(57) ABSTRACT

Technology for semantic compression is disclosed. In various embodiments, the technology receives data that represents one or more physical attributes sensed by one or more sensors; employs at least one pattern or statistical feature to identify a first region and a second region in the received data; computes a first utility and a first relevant feature for the first region, and a second utility and a second relevant feature for the second region; and identifies based on at least the first utility and the second utility a first compression method to apply to the first region and a second compression method to apply to the second region wherein the first and the second compression methods have different compression rates, different feature preservation characteristics, or both.

26 Claims, 7 Drawing Sheets

(56) References Cited

U.S. PATENT DOCUMENTS

| | | | |
|---|---|---|---|
| 5,506,916 A | 4/1996 | Nishihara et al. | |
| 5,868,669 A | 2/1999 | Iliff | |
| 7,643,142 B2 | 1/2010 | van den Engh | |
| 7,653,248 B1 | 1/2010 | Witzgall et al. | |
| 8,868,476 B2 | 10/2014 | Potkonjak | |
| 2002/0103938 A1* | 8/2002 | Brooks | H03M 7/30 709/247 |
| 2003/0012400 A1 | 1/2003 | McAuliffe et al. | |
| 2003/0158468 A1 | 8/2003 | Iliff | |
| 2003/0212319 A1 | 11/2003 | Magill | |
| 2004/0049598 A1* | 3/2004 | Tucker et al. | 709/246 |
| 2004/0068332 A1 | 4/2004 | Ben-Gal et al. | |
| 2005/0049497 A1 | 3/2005 | Krishnan et al. | |
| 2005/0078017 A1 | 4/2005 | Gergely et al. | |
| 2005/0131660 A1 | 6/2005 | Yadegar et al. | |
| 2005/0244069 A1 | 11/2005 | Wang | |
| 2005/0256974 A1 | 11/2005 | Teodosiu et al. | |
| 2005/0265616 A1 | 12/2005 | Rose | |
| 2006/0063156 A1* | 3/2006 | Willman | C12Q 1/6886 435/6.14 |
| 2006/0104526 A1 | 5/2006 | Gringeler et al. | |
| 2006/0129324 A1* | 6/2006 | Rabinoff | A61B 5/048 702/19 |
| 2006/0224059 A1 | 10/2006 | Swedlow et al. | |
| 2007/0004466 A1 | 1/2007 | Haartsen | |
| 2007/0079223 A1 | 4/2007 | Mondin et al. | |
| 2007/0096954 A1 | 5/2007 | Boldt et al. | |
| 2007/0127793 A1* | 6/2007 | Beckett et al. | 382/128 |
| 2007/0233623 A1 | 10/2007 | Vatchkov et al. | |
| 2008/0004904 A1 | 1/2008 | Tran | |
| 2008/0050025 A1 | 2/2008 | Bashyam et al. | |
| 2008/0187047 A1 | 8/2008 | Stephan et al. | |
| 2008/0243208 A1* | 10/2008 | Corndorf | A61N 1/025 607/60 |
| 2009/0037220 A1 | 2/2009 | Chambers et al. | |
| 2009/0069642 A1 | 3/2009 | Gao et al. | |
| 2009/0124917 A1 | 5/2009 | Hatlestad et al. | |
| 2009/0177495 A1 | 7/2009 | Abousy et al. | |
| 2009/0228299 A1 | 9/2009 | Kangarloo et al. | |
| 2009/0312817 A1 | 12/2009 | Hogle et al. | |
| 2010/0008424 A1 | 1/2010 | Pace | |
| 2010/0030087 A1* | 2/2010 | Hettrick | A61B 5/02158 600/485 |
| 2010/0046848 A1 | 2/2010 | Witzgall et al. | |
| 2010/0063365 A1 | 3/2010 | Pisani et al. | |
| 2010/0076714 A1 | 3/2010 | Discenzo | |
| 2011/0251986 A1 | 10/2011 | Potkonjak | |
| 2012/0265737 A1 | 10/2012 | Potkonjak | |
| 2013/0041861 A1 | 2/2013 | Potkonjak et al. | |

OTHER PUBLICATIONS

Didier Le Gall, "Mpeg: a Video Compression Standard for Multimedia Applications," Communications of the ACM, V. 34 n. 4, Apr. 1991, pp. 46-58.

Doukas et al., "Context-Aware Medical Content Adaptation through Semantic Representation and Rules Evaluation," 3rd International Workshop on Semantic Media Adaptation and Personalization, 2008, 22 pages.

Gallager, R., "Variations on a Theme by Huffman," IEEE Transactions on Information Theory, vol. IT-24, No. 6, Nov. 1978, 7 pages.

Huffman, David A., "A Method for the Construction of Minimum-Redundancy Codes," Proceedings of the I.R.E, 40, 9, September, 1098-1101.

International Search Report and Written Opinion; International Application No. PCT/US10/30950; Filed Apr. 13, 2010; Applicant: Empire Technologies Development LLC; dated Sep. 23, 2010; 10 pages.

Sahay et al., "Semantic Annotation and Inference for Medical Knowledge Discovery," NSF Symposium on Next Generation of Data Mining, 2007, Baltimore NSF Symposium Processings, 5 pages.

Shapiro, J., "Embedded Image Coding Using Zerotrees of Wavelet Coefficients," IEEE Transactions on Signal Processing, vol. 41, No. 12, Dec. 1993, 18 pages.

Wallace, Gregory K., "The JPEG Still Picture Compression Standard," Digital Equipment Corporation, Maynard, Massachusetts, Dec. 1991, 17 pages.

Ziv et al., "A Universal Algorithm for Sequential Data Compression," IEEE Transactions on Information Theory, vol. IT-23, No. 3, May 1977, 7 pages.

"Electronic Implants that Dispense Medicines Via Wireless Medical Network are on the Horizon," Feb. 6, 2009. http://www.azonano.com/news.aspx?newsID=9780.

Anderson et al, "Shakra: tracking and sharing daily activity levels with unaugmented mobile phones," Mobile Networks and Applications, v.12 n.2-3, p. 185-199, Mar. 2007.

Bai et al. "Segmentation-based multilayer diagnosis lossless medical image compression" Australian Computer Society, Inc. Darlinghurst, Australia, Australia 2004.

Consolvo, Sunny et al., "Design requirements for technologies that encourage physical activity," Proceedings of the SIGCHI conference on Human Factors in computing systems, Apr. 2006.

Danninger et al., "The connector: facilitating context-aware communication," Proceedings of the 7th Int'l conference on Multimodal Interfaces, Oct. 2005.

Driver, Cormac and Siobhan Clarke, "An application framework for mobile, context-aware trails," Pervasive and Mobile Computing, v.4 n.5, p. 719-736, Oct. 2008.

Hand, E., "Head in the clouds," Nature, vol. 449, Oct. 24, 2007, p. 963.

Harrison, Chris et al., "Lightweight material detection for placement-aware mobile computing," Proceedings of ACM symposium on User interface software and technology, Oct. 2008.

Hayes, Brian, "Cloud computing," Communications of the ACM, v.51 n.7, Jul. 2008.

Iso et al., "Gait analyzer based on a cell phone with a single three-axis accelerometer," Proceedings of the 8th conference on Human-computer interaction with mobile devices and services, Sep. 2006.

Istepanian, R.S.H. and S. Laxminaryan, "UNWIRED, the next generation of wireless and internetable telemedicine systems-editorial paper," IEEE Trans. Inform. Technol. Biomed., vol. 4, pp. 189-194, Sep. 2000.

Jovanov, E. et al., "Stress monitoring using a distributed wireless intelligent sensor system," IEEE Eng. Med. Biol. Mag., vol. 22, No. 3, pp. 49-55, May/Jun. 2003.

Kanefsky, M. & C-B Fong, "Predictive source coding techniques using maximum likelihood prediction for compression of digitized images," IEEE Transactions on Information Theory, vol. 30, Issue 5, pp. 722-727, Sep. 1984.

Khalil et al., "Context-aware telephony: privacy preferences and sharing patterns," Proceedings of the conference on Computer supported cooperative work, Nov. 2006.

Korhonen, I. et al., "Health monitoring in the home of the future," IEEE Eng. Med. Biol. Mag., vol. 22, No. 3, pp. 66-73, May/Jun. 2003.

Kurdi, Heba et al., "A Classification of Emerging and Traditional Grid Systems," IEEE Distributed Systems Online, v.9 n.3, p. 1, Mar. 2008.

Lederer, Scott et al., "Personal privacy through understanding and action: five pitfalls for designers," Personal and Ubiquitous Computing, v.8 n.6, p. 440-454, Nov. 2004.

Ogiela et al. "Nonlinear processing and semantic content analysis in medical imaging—a cognitive approach" Inst. of Autom.s, AGH Univ. of Sci. & Technol., Krakow, Poland, Dec. 2005.

Park, S. and S. Jayaraman, "Enhancing the quality of life through wearable technology," IEEE Eng. Med. Biol. Mag., vol. 22, No. 3, pp. 41-48, May/Jun. 2003.

Pattichis, C. S. et al., "Wireless telemedicine systems: An overview," IEEE Antennas Propagat. Mag., vol. 44, No. 2, pp. 143-153, Apr. 2002.

Rissanen, J. "Generalised Kraft inequality and arithmetic coding" IBM J. Res. Dev. 20, 198-203, 1976.

(56) References Cited

OTHER PUBLICATIONS

Robison, S., "A Bright Future in the Cloud," Financial Times, Mar. 4, 2008.
Rochwerger, B. et al., "The reservoir model and architecture for open federated cloud computing," IBM Systems Journal, vol. 53, No. 4, 2009.
Siewiorek et al., "A Context-Aware Mobile Phone," Proceedings of the 7th IEEE Int'l Symposium on Wearable Computers, pp. 248-249, 2003.
Stanford, V., "Using pervasive computing to deliver elder care," IEEE Pervasive Computing, vol. 1, pp. 10-13, Jan./Mar. 2002.
Valdastri, P. et al., "An implantable telemetry platform system for in vivo monitoring of physiological parameters," IEEE Trans. Inform. Technol. Biomed., vol. 8, No. 3, pp. 271-278, Sep. 2004.
Witten et al. "Arithmetic coding for data compression," Communications of the ACM, v.30 n.6, p. 520-540, Jun. 1987.
Zhang et al., "An on-line universal lossy data compression algorithm via continuous codebook refinement. I. Basic results," Information Theory, IEEE Transactions on, vol. 42, pp. 803-821, 1996.
U.S. Appl. No. 12/996,972, filed Oct. 18, 2011, Potkonjak.
International Search Report for PCT/US10/30953, Filed Apr. 13, 2010; Applicant: Empire Technologies Development LLC, dated Aug. 4, 2010.
International Search Report for PCT/US2010/030954 filed Apr. 13, 2010; Applicant: Empire Technology Development, LLC; dated Aug. 25, 2010.
International Search Report for PCT/US2010/030952 filed Apr. 13, 2010; Applicant: Empire Technology Development LLC, dated Dec. 12, 2011.

* cited by examiner

SEMANTIC COMPRESSION

CROSS-REFERENCE TO RELATED APPLICATIONS

This application is a U.S. National Stage application under 35 U.S.C. §371 of International Application No. PCT/US2010/030953, filed on Apr. 13, 2010, entitled "ADAPTIVE COMPRESSION," which is related to U.S. patent application Ser. No. 12/966,010, filed on Dec. 2, 2010, entitled "COMBINED-MODEL DATA COMPRESSION," all of which are incorporated herein by reference in their entireties.

BACKGROUND

Many fields of human endeavor now use computing devices. Some of these fields collect and process vast amounts of data. As an example, medical data can grow exponentially. A medical facility may attach several sensors to an ailing or recovering patient, e.g., heart rate monitor, blood pressure monitor, electrocardiograph (EKG) monitor, blood content monitor, urine analysis monitor, brain activity monitor, various other electrodes, etc. When samples are taken from these sensors at a high frequency, the data storage requirements can become immense.

Some of this collected data can require many thousands of terabytes of data storage space, if not more. It is now commonplace for even home computer users to purchase hard disk drives (HDDs) for personal computing devices that provide a storage capacity of 1 terabyte or more. To reduce the amount of storage space that is needed to store data, various compression methods exist. Compression methods use a fewer number of bits to store data than the number of bits that represent the uncompressed data. Compressed data can thus require less storage space to store and reduced network bandwidth to transmit the compressed data as compared to the equivalent data prior to compression ("uncompressed data").

Many compression methods, including compression methods used to compress medical data, are often selected without regard to the use or semantics of the underlying original data. For example, compression methods may be selected for some specified level of encoding to preserve values within a specified margin of error. The former may be termed lossless compression and the latter may be termed lossy compression. Lossless compression enables the compressed data to be expanded with full fidelity. However, this is done at the cost of storage space or network bandwidth. In contrast, lossy compression may need less space than lossless compression, but expanding the compressed data may not reproduce the original uncompressed data with as much fidelity as a lossless compression method.

SUMMARY

Technology for semantic compression is disclosed. In various embodiments, the technology receives data that represents one or more physical attributes sensed by one or more sensors; employs at least one pattern or statistical feature to identify a first region and a second region in the received data; computes a first utility and a first relevant feature for the first region, and a second utility and a second relevant feature for the second region; and identifies based on at least the first utility and the second utility a first compression method to apply to the first region and a second compression method to apply to the second region wherein the first and the second compression methods have different compression rates, different feature preservation characteristics, or both.

DETAILED DESCRIPTION

Figure 1:
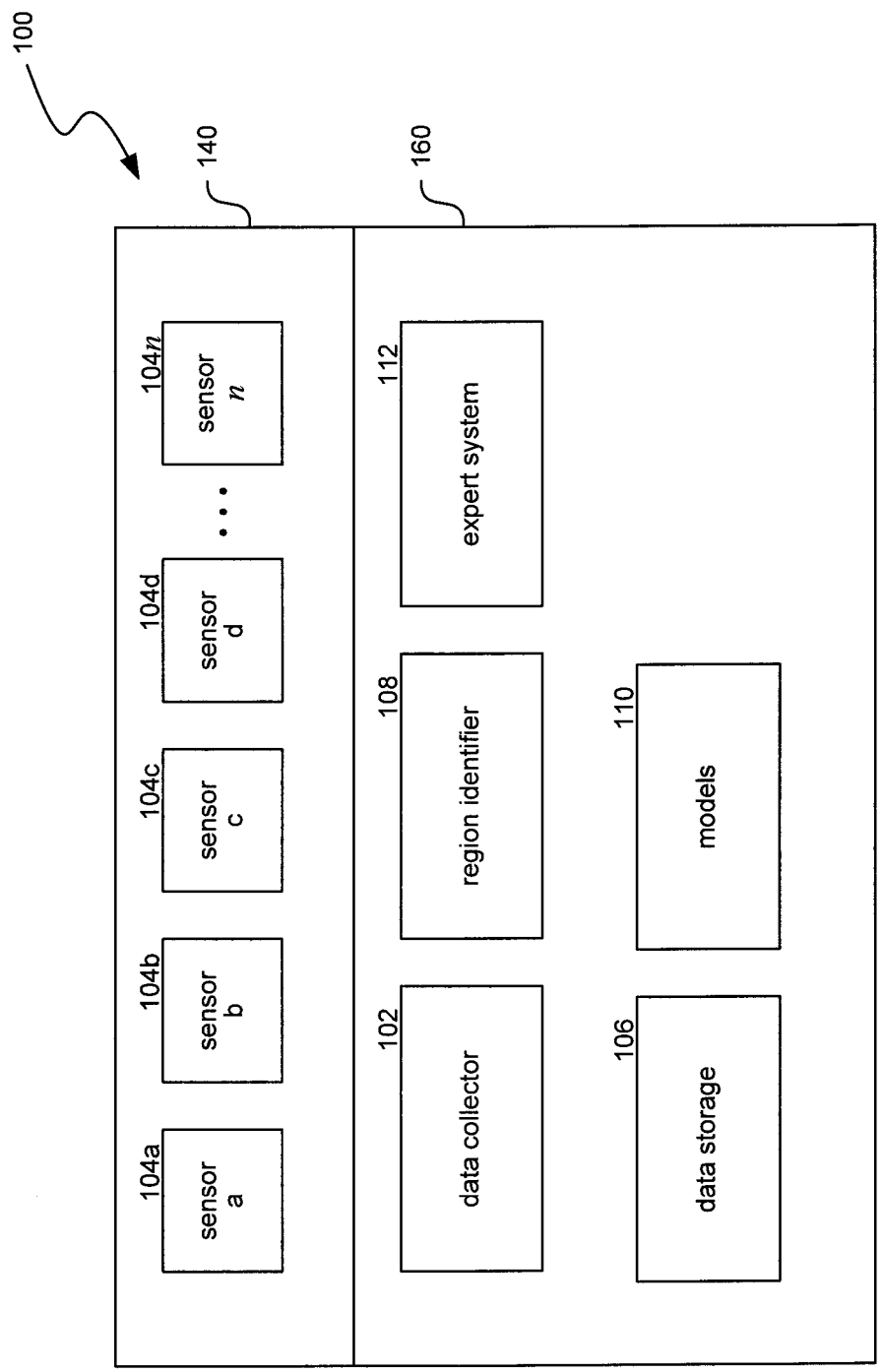
FIG. 1 is a block diagram illustrating an environment in which a semantic compression technology may operate in some embodiments.

Semantic compression technology is disclosed. In various embodiments, the semantic compression technology identifies information—either explicitly or implicitly—derived from physical, chemical, biological, and medical laws that govern signals recorded by sensors (e.g., sensors deployed proximate to medical patients) and leverages the identified information to determine to what extent a particular feature in the original and compressed signal is important for actual medical use.

Various sensors are often used to collect data, e.g., medical data from patients. The signals from these sensors can be either collected digitally or converted to digital numeric form, e.g., by using an analog-to-digital converter. The collected data can then be stored, such as by a computing device. Semantic awareness of the data can be beneficial in improving the analysis and/or compression of this data. Three observations are provided herein, but various embodiments of the disclosed technology may be capable of operating whether or not one or more of these observations hold true for any particular patient. (I) Data can have a level of similarity that makes it possible to treat different values as equivalent values. As an example, it may be beneficial to know that two values (e.g., 120 and 121 for the systolic portion of a blood pressure reading) are so similar that no meaningful difference exists between the two. Thus, a common symbol can be used during compression to represent both 120 and 121. (II) The collected data may also have a high correlation between the sensed values. As an example, as the temperature of a patient or the ambient temperature changes, the systolic portion of a blood pressure reading of the patient may also change in a predictable manner. When multiple sensors are applied to a patient, values collected from the sensors may thus be correlated, e.g., based on the patient's medical condition. The data (and/or predicted data) from any two sensors may be asymmetric, and so deciding the relative order in which sensed signals are mutually predicted and compressed as well as how much to relatively shift each signal can greatly improve compression ratios or preservation of important features ("feature preservation characteristics") of the initial signals. (III) Because the sensed data are the result of physical, chemical, and biological phenomena, they may not occur randomly. As an example, it is rare for a patient's blood pressure or temperature to jump randomly. Indeed, it is more likely for there to be gradual changes. Such signals may be more easily capable of prediction (and therefore optimized compression) if the phenomena are at least partially understood and characterized. As an example, consider sensors deployed in an athletic device, such as a shoe. There are three natural phases for an athlete when walking, running, or jumping: taking off, landing, and airborne. When taking off and landing, the pressure on sensors decrease or increase, respectively. In such cases, delta compression techniques may perform well. When airborne, the pressure is zero on all sensors and therefore run-length encoding or other compression technique that records only non-zero (or zero) samples may be superior.

In various embodiments, the semantic compression technology can employ semantic (e.g., relevant for accurate diagnosis or treatment) and context (e.g., geolocation and physical time) information. A first phase is a learning and characterization phase. In this phase, the technology can employ a computing system to (i) analyze already collected and preprocessed data and diagnosis results to identify a system of signal features that are most relevant for correct diagnosis; (ii) employ statistical and/or artificial intelligence techniques to process, analyze and optionally verify the utility of the features; and (iii) employ pattern matching and statistical algorithms to segment the signal into two or more segments (e.g., regions) in such way that in each of the segments, data has the same utility and/or requirements for preservation of a system of features.

A second phase is an operational phase. In this second phase, the semantic compression technology employs results of the learning phase to automatically segment one or more signals in such a way that its utility and most relevant features guide the selection of the selected compression methods that achieve Pareto optimal compression rate, e.g., for utility tradeoff or other related objective. In some embodiments, the technology coordinates the selection for all the segments (e.g., regions of data) using dynamic programming techniques.

In various embodiments, the semantic compression technology can identify boundaries of regions of information; identify an optimal compression technique for each region; estimate what is required in a following compression session; identify how to make use compression rates while preserving the important features of the collected data; and identify how to organize recursive application of segmentation (e.g., by "partitioning" of data into regions by identifying boundaries). Various techniques the semantic compression technology employs to implement each of these steps will now be described in more detail. However, one skilled in the art will understand upon reading this detailed description that the disclosed technology can be readily adapted for use with other techniques, whether similar or disparate.

Various techniques can be employed to identify boundaries. In some embodiments, a human expert can initially specify important ("high utility") regions in data and features that make the regions important, and then pattern matching algorithms can identify the regions automatically in data received from sensors. In some embodiments, a human expert can specify the high utility regions, and statistical and machine learning techniques can identify relative features that make the regions important, and then pattern matching algorithms can identify the regions automatically in data received from sensors. In some embodiments, the semantic compression technology employs parametric and non-parametric statistical techniques to analyze diagnosis reports and corresponding data to identify high correlation features for each potential disease (e.g., diagnosis), statistical and machine learning techniques to find relative features that make the regions important, and pattern matching algorithms to identify the regions in the signals.

To identify an optimal compression technique for each region, the semantic compression technology employs in various embodiments statistical techniques that measure various signal properties, e.g., entropy, entropy that tolerates a given error, and autocorrelation with experimentally observed compression rates for a set of compression techniques on data with similar properties.

To estimate what is required in a following compression session, the semantic compression technology can follow (e.g., receive input on or determine) common disease progression trends (e.g., in data received from sensors) and deduce which type of compression is most likely most effective.

To identify how to make use compression rates while preserving the important features of the collected data, the semantic compression technology in various embodiments can employ statistical techniques that measure various signal properties, e.g., entropy, entropy that tolerates a given error, and autocorrelation with experimentally observed ability to preserve targeted features for a set of compression techniques on data with similar properties.

To identify how to organize recursive application of segmentation, the semantic compression technology in various embodiments can employ iterative searching. As an example, semantic compression technology creates a set of techniques for the first level, and then another set at each subsequent level, and identify a subset of the best multilevel results.

In various embodiments, the semantic compression technology may identify a compression method to apply to a region of data by employing a dynamic programming technique. Dynamic programming involves first mapping a problem into a graph theoretic domain wherein for each region of data, there are $k_i$ alternative compression methods, each with compression rate $r_i$ and utility $u_i$. The dynamic programming technique finds a path from a node that connects to all options for the first region to a node that has incoming edges from all nodes at a previous level that has the highest compression rate for a specified sum of utilities or vice versa.

In various embodiments, the technology receives data that represents one or more physical attributes sensed by one or more sensors; employ at least one pattern or statistical feature to identify a first region and a second region in the received data; compute a first utility and a first relevant feature for the first region, and a second utility and a second relevant feature for the second region; and identify based on at least the first utility and the second utility a first compression method to apply to the first region and a second compression method to apply to the second region wherein the first and the second compression methods have different compression rates or different feature preservation characteristics. The technology can identify the first and second regions comprises by characterizing a utility of different signal segments; identifying a unique combination of features in each segment; and deriving one or more algorithms for automatic feature identification using a pattern matching technique, statistical technique, or both a pattern matching technique and a statistical technique. The characterizing can include analyzing one or more sets of diagnosis results. An identification of the unique combination can be received, e.g., from a human expert. The analysis may be done by a human expert or an expert system. The analyzing and/or the deriving can include employing one or more dynamic programming pattern matching or statistical techniques. The identifying can include employing a statistical technique. The deriving can include employing a combinatorial or numerical pattern matching technique. The technology can repeat the characterizing, identifying, and deriving until a resulting model does not pass a learn and test criterion or a resubstitution test, e.g., a jackknife test. At least one of the first and the second compression methods can be selected by comparing at least one of the different compression rates or different feature preservation characteristics after applying the compression methods to two or more sets of data (e.g., data derived from one or more sensors). The technology may build a statistical model based on the application of the compression methods to the two or more sets of data and employing the statistical model to select the compression methods. The data may be preprocessed using one or more signal processing techniques. The signal processing technique can be at least one of a linear transformation or a difference-based technique. When the first utility is higher than the second utility, the first compression method can be lossless and the second compression method can be lossy. The technology may iteratively identify additional regions in the data until a stopping criterion is satisfied. Examples of stopping criteria are running time of the overall procedure exceeding a threshold specified value, lack of compression rate improvement, etc. The technology may identify a compression method for each segment by applying a dynamic programming technique. The technology may perform steps for receiving data from one or more signals corresponding to one or more sensors; selecting one or more signals for semantic compression; partitioning the selected signals into one or more regions; and selecting a compression method for each region. The technology may control the identification of a compression method for the first region by specifying the first utility using a joint utility function wherein the joint utility function indicates a relative utility of the first region if the second utility of the second region has a particular value. The first region can relate to a first signal from a first sensor and the second region relates to a second region from a second sensor. The utility and the joint utility functions can be defined using probability density functions. The utilities can be combined using maximum likelihood expectation (MLE), minimal mean-square expected error (MSEE), multiple explanation variable statistical models, or other statistical techniques. The technology can receive an iteratively updated patient diagnosis wherein the first utility is computed based on a previous patient diagnosis and the second utility is computed based on a current patient diagnosis. The technology can receive external data and modify the updated patient diagnosis based on the external data. Examples of the external data are geolocation, physical time, a recent activity of the patient, etc. The external data can be a statistical or a numerical quantification of a current or recent epidemic.

A large number of sensors can be used for medical applications, ranging from simple temperature measurement devices to high resolution multiple slices scanners that are capable of producing many gigabytes of data even in a single session. Compression can be important in remote treatment applications, e.g., to reduce bandwidth and latency issues. Semantic compression can be employed wherein each segment (e.g., partition) of data from each type of sensor can be compressed using lossless or lossy compression methods in such a way that the impact of the compression on the most beneficial treatment is zero or at least minimal for a given level of compression. The technology may employ a human expert, statistical techniques, and/or information theory techniques to determine to what extent a particular segment of data is relevant for the treatment of the patient.

The technology can (a) receive or make a current medical diagnosis; (b) receive or make a medical prediction; (c) receive or make an identification of symptoms; (d) label data or receive labeling; (d) create one or more utility functions; (e) calculate compression levels versus error characterizations for each segment; and (f) selecting the compression technique and level for each segment (e.g., partition). One or more of the steps (e.g., (a), (b), and (c)), may be option in various embodiments. Various information may be determined by the technology or received, e.g., from another system, a human expert, or an expert or statistical diagnosis system.

The diagnosis can cover not only the current patient status, but also the most likely or comprehensive progression predictions for the patient. The predictions can be static where the predictions are not dependent on the recorded sensor data. An alternative is to use dynamic predictions that are triggered and considered as actual potential predictions only after a specific set of events detected in sensor signal streams is observed. The diagnosis may be generic, specific for a class of patients, or specific for an individual patient. The diagnosis may change even without sensed data. For example, the report on the status of epidemic data collected manually or new insights into the relevant disease may cause the change of the diagnosis and/or the predictions of the future potential diagnoses.

Once the diagnosis is available, the technology can use data labels from the same or other patients that are subject to the identical or similar diagnoses. The labeling can be binary (important or unimportant) or specified using numeric or symbolic characterization. In addition, the label or annotation may include the utilities or conditional utilities of having a particular signal with a particular level of utility. Also, the benefits can be a function of and dependent on the amount of already collected information of particular quality.

There are several options for labeling data, e.g., a human (expert) conducts manual labeling; machine learning, statistical techniques or heuristics can be applied for automatic labeling after an initial training phase. For example, the properties of data streams can be used as indicators of importance. The labeling can be optimistic, pessimistic, or done using a user-specified strategy. In the pessimistic strategy, all samples are labeled with the highest utility unless explicit indicators for lowering the importance are detected. The properties may be independent or conditional. For example, conditional importance may be that if a signal A has a specified property then signal B has the lowest utility. Finally, the importance assignment may be influenced by the detection of a particular pattern in the sensed signals.

The utility function creation step assigns a utility to a time segment as a function of the level of lossy compression that is used for the time segment. The technology evaluates time segmentation and the identification of a utility score in the presence of noise. The technology attempts to create time segments of each signal where the utility function is constant. In various embodiments, the technology may employ (i) motif (pattern) scanning; (ii) unsupervised learning; (iii) supervised learning; and (iv) maximum likelihood.

In the first technique the technology can scan time signals to find one or more types of patterns. In some embodiments, the technology permits patterns to differ from the template according to a user specified error measure by a specific amount. For example, motif may be the first local maximum in the signal after the local maximum that is at least a specified amount over the average value of the signal. Once the first local maximum is identified, the technology can include a specified number of previous and consequent number of symbols.

The second technique is clustering, wherein the technology segments time signals according to a set of rules. For example, the technology can partition the time signal. Alternatively, each segment can comprise a pair of monotonically non-decreasing and monotonically non-increasing segments. On each part of the segmented signal, the technology may apply an unsupervised learning technique (e.g., clustering) according to a user specified distance measure. For example, the technology can use a k-nearest neighbors mechanism to decide to which group of signals (with which priority) a pertinent signal segment should be assigned. Alternatively, the technology may use a supervised learning (regression) to predict the utility. Finally, the technology may use a maximum likelihood procedure to combine multiple predictions for assigning utility functions. The technology in various embodiments can employ both parametric and non-parametric statistical techniques (e.g., motif (pattern) scanning; clustering; regression; supervised learning; maximum likelihood from multiple characterizations; etc.)

After assigning utilities to each segmented level, the technology finds the most suitable compression method for each specified error of compression rate. In various embodiments, the technology can use a probability distribution or density function of the class of segments and estimate the rate of compression using entropy and conditional entropy. Alternatively, the technology can apply a subset of typical compression methods and use the best obtained compression as the estimate. The actually applied compression method does not have to be same as the best obtained estimate, and the technology can continue a computationally intensive search for the better compression method guided by the compression rates of representative methods. The technology can create statistical models using either the properties of the signal segment or the performance of the executed compression algorithms to predict the compression level vs. error curve.

Diagnosis-based selection can be used to allocate the compression levels that are functions of allowed compression errors to each time segment. The technology attempts to maximize the overall utility for a specified compression rate and optimize compression rates while the level of utility is above the specified level. The technology may also employ Pareto optimal options, e.g., to assign compression errors to the segments having no other assignment that is simultaneously better both in utility and compression level. The technology may assign a set of utility levels to each segment for a corresponding set of error levels. If the relationship between the utility level can be approximated using monotonic piecewise linear functions or convex functions, the technology can solve the problem using linear programming and convex programming respectively. Otherwise, the problem can be solved using knapsack problem algorithms or nonlinear programming.

Thus, the technology is capable of simultaneously compressing several signals. The technology can process the native signal (e.g., from a sensor) before compressing the data. For example, the technology can use delta-transformation or any orthogonal transformation such as Fourier or discrete cosine transform.

In various embodiments, the semantic compression technology is capable of selecting different suitable compression methods for data or regions of the data. As an example, the semantic compression technology may select a compression method based on a preliminary diagnosis of a patient. The preliminary diagnosis can be specified by a user (e.g., physician, nurse, etc.) or detected automatically, such as by using an expert system. In some embodiments, the semantic compression technology can select a suitable compression method for data based on the diagnosis and a corresponding model. As an example, when a patient is diagnosed with a particular disease and a model is defined for the disease, the semantic compression technology can use the compression method suitable for the model. The semantic compression technology may be capable of doing this because two patients having similar health conditions are likely to have similar biophysical characteristics, though perhaps of varying scale. The implementation of the semantic compression technology is not limited by this observation, however.

The compression method may have been previously defined or may be dynamically selected (e.g., based on how well the data is capable of being compressed). The model may specify, for one or more diseases, which data is more important than other data. As an example, heart rate, heart rhythm, and blood pressure may be more important for cardiac disease patients than iron content in blood. In such a case, when a patient is preliminarily diagnosed as being a cardiac disease patient, the semantic compression technology may compress heart rate, heart rhythm, and blood pressure with lossless compression and iron content with lossy compression. In various embodiments, the semantic compression technology can identify regions of the data that may be more important than other regions. As an example, a first portion of heart rhythm data may be more important than a second portion. The semantic compression technology may then compress the more important regions using a first compression method (e.g., a lossless method) and the less important regions using a second compression method (e.g., a lossy method). Thus, the semantic compression technology may employ storage space more efficiently than completely lossless compression methods, yet may be able to expand important regions of data that has been compressed with higher fidelity than lossy compression methods.

In various embodiments, regions of data can be portions of data from a single sensor or from multiple sensors. As an example, data from a heart rate monitor can be a first part and data from a blood pressure monitor can be a second part. Alternatively, various portions of data from an EKG can be separate parts. One skilled in the art will understand that data can be apportioned into different regions in multiple different ways.

The semantic compression technology may employ models (e.g., semantic models) that describe the data. As an example, a model may describe that the data to be compressed relates to information sensed from EKG sensors. The model may specify the relative importance of different regions of the data. The model may also specify which compression methods to use for each region. The model can be defined statically, conditionally, or interactively.

In static model definitions, the model may a priori specify which regions of the data are important. As an example, a static model may specify that data collected from a patient preliminarily diagnosed as having cardiac arrhythmia should use a lossless compression method for a P-wave region of the EKG signal and a lossy compression method for the remaining regions (e.g., Q-, R-, S-, and T-wave regions) of the EKG signal.

In conditional model definitions, the model may specify that the importance of regions may depend on the data to be compressed. As an example, a healthy patient's heart rate may normally be compressed using a lossy compression method because the heart rate will typically not fluctuate significantly when the patient is sitting in a chair or lying in bed. A conditional model may specify that if the healthy patient's heart rate does fluctuate significantly, it should be compressed using a lossless compression method.

In interactive model definitions, a user or an automated process may specify which regions of data are more important than other regions. As an example, a physician or scientist may specify that a particular region of data is more important than another region of data. Alternatively, an expert system or some other automated process may specify that a particular region of data is more important than another region of data. As an example, the user or expert system may specify regions of important data based on a preliminary diagnosis of a patient. In some embodiments, the expert system may also first determine what the preliminary diagnosis is based on the data to be compressed.

The semantic compression technology may identify bounds of a region and a utility value for each bounded region. A bound of a region can be identified based on an understanding of the underlying data. As an example, bounds of an EKG can be used to identify a P-, Q-, R-, S-, and/or T-wave regions of an EKG signal. The bounds can be identified based on specified criteria for the bounds. As an example, the criteria for an EKG signal may specify that a P-wave is that region of the EKG signal preceding a local low (Q) of the EKG signal immediately preceding a high point of the EKG signal (R).

The semantic compression technology may then receive a utility value for each region. A utility value for a region of data can represent a relative importance of the region as compared to other regions of the data. The utility can be based on a preliminary diagnosis of the patient. As an example, the P-wave region of an EKG signal may have a higher utility for a patient with cardiac arrhythmia than other regions of the EKG signal. In contrast, the T-wave region of the EKG signal may have a higher utility for a patient with coronary ischemia or central nervous system disorders than other regions of the EKG signal.

The semantic compression technology can associate a model with each preliminary diagnosis. The model can specify how to identify regions of data (e.g., bounds for each region) and the utility for each region. The model can also specify which compression method to use for each region.

In some embodiments, the semantic compression technology can be deployed in medical environments. In such environments, some patients can receive a preliminary diagnosis of being healthy while other patients may receive a preliminary diagnosis of being ill (i.e., unhealthy). The healthy or ill classifications may be received for certain regions of the patient's body. For example, a heart patient may have healthy lungs but an unhealthy heart, whereas an ulcer patient may be completely healthy everywhere but in the digestive tract. Different sensors may be attached to patients to collect data, such as during a routine physical checkup or an extended hospital stay. The sensors may be attached to the patient's skin or other parts of the patient's body. The semantic compression technology may employ the preliminary diagnosis to select various compression methods. For example, the semantic compression technology may select a lossless compression method to compress heart-related data for the heart patient, but may select a lossy compression method to compress other data. The semantic compression technology may also select compression methods on a more granular basis. As an example, the heart patient may be preliminarily diagnosed as having cardiac arrhythmia. In such a case, a model may indicate that a P-wave region of the patient's EKG reading is more important than other regions of the EKG reading. The semantic compression technology may then compress regions of the EKG signal other than the P-wave region using a lossy compression method and may compress the P-wave region using a lossless compression method.

In various embodiments, the semantic compression technology can receive from a user or determine, e.g., using an expert system (a) a preliminary medical diagnosis for a patient; (b) a medical prediction for the patient; and (c) an identification of symptoms. The semantic compression technology may then (d) identify regions of data; create a utility function; and (f) identify appropriate compression methods for each region of data.

The preliminary medical diagnosis may be generic, specific for a class of patients, or specific for an individual patient. The diagnosis may change based on one or more factors external to the patient. As an example, a report on the status of epidemic data or new insights into a disease relevant to the patient's prior diagnosis of a disease may cause the change of the diagnosis for one or more patients. As an example, if a patient has a high fever, coughing, and respiratory difficulty and is in an area where there is an influenza epidemic relating to a particularly virulent variety (e.g., "H1N1"), the semantic compression technology may change the diagnosis for one or more patients to indicate the influenza. If a patient has received a preliminary diagnosis of cardiac arrhythmia and research indicates that mild temperature associated with cardiac arrhythmia is indicative of a specific other problem, the semantic compression technology may change the diagnosis for a cardiac arrhythmia patient who has a mild temperature to identify the specific other problem.

The medical predictions can be static or dynamic. When a medical prediction is static, it may not depend on data recorded from sensors about the patient. When the medical prediction is dynamic, it may be triggered by a set of events occurring in the data recorded from the sensors.

The semantic compression technology may then annotate the recorded data for the patient using a model or other prior diagnoses that are similar. The annotations can be binary (e.g., "important" or "unimportant") or can be specified using numeric or symbolic characterization. In addition, the annotations may specify the utilities or conditional utilities. In various embodiments, the annotations can be applied manually or automatically. As an example of manual application, a user can apply the annotations. As an example of automatic application, the semantic compression technology may automatically apply annotations, for example, by employing techniques such as machine learning, statistical techniques or heuristics after an initial "machine learning" period. The annotations can be applied using an optimistic, a pessimistic, or a user-specified strategy. In the optimistic strategy, some regions of data (e.g., data from some sensors) are annotated with a high utility value. In the pessimistic strategy, all regions of data are labeled with the highest utility unless an explicit indicator for lowering the importance is detected. In the user-specified strategy, a user can set or reset the utility values. These annotations may be specified independently or conditionally. As an example of conditional specification, if a region of data recorded from a first sensor has a specified property, a region of data may receive a high utility. The utility for a region of data may also be influenced by detection of a pattern in the data.

The utility can be specified as a function of the level of "lossiness" of the compression that is used for a region (e.g., time segment). In various embodiments, the semantic compression technology attempts to identify time segments to divide the recorded data such that the utility function remains constant within each time segment. To do this, the semantic compression technology can employ (i) motif (or pattern) scanning; (ii) unsupervised learning; (iii) supervised learning; and/or (iv) maximum likelihood. In motif scanning, the semantic compression technology can scan the recorded data to find one or more types of patterns in the data. As an example, the motif may be the first local maximum in the signal from a sensor after the local maximum that is at least a specified amount more than the average value of the signal. In unsupervised learning, the semantic compression technology may segment the data into regions according to a set of rules. As an example, it can cluster the data so that each segment includes data near a value and a specified count of the nearest neighboring data samples may be assigned to that segment. In supervised learning, the semantic compression technology can employ support vector machines or other machine learning techniques to divide the data. The semantic compression technology may use maximum likelihood estimation procedures to combine multiple predictions for assigning utility functions.

After assigning utility to each of the regions of data, the semantic compression technology can attempt to find the most suitable compression method for each specified error of the compression rate for each region of data. In various embodiments, the semantic compression technology can employ probability distribution functions to estimate the rate compression using entropy or conditional entropy, apply a subset of typical compression methods and use the best obtained compression as the estimate, etc.

The semantic compression technology may select a compression method that satisfies various objectives, e.g., reduced storage space, low error, etc. In various embodiments, the semantic compression technology may attempt to maximize the overall utility for a specified compression rate. A compression rate can be expressed as the comparison between the original uncompressed data and the compressed data. The semantic compression technology may attempt to optimize the compression rate while still keeping the utility value above a specified value, e.g., by using Pareto optimization, knapsack optimization, linear programming, nonlinear programming, or other techniques generally known in the art.

The technology will now be described with reference to the Figures ("drawings"). In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

FIG. 1 is a block diagram illustrating an environment 100 in which a semantic compression technology may operate. In various embodiments, environment 100 can include one or more sensors 140 and components 160. Sensors 104a-104n are shown in sensors 140 by way of example and one skilled in the art will appreciate that there may be a different number of sensors in sensors 140. As examples, sensors 104A, 104B, and 104C may receive a patient's EKG signals; sensor 104D may receive the patient's temperature; and sensor 104n may receive data about the patient's blood content. Components 160 can include a data collector 102, a data storage 106, a region identifier 108, models 110, and an expert system 112. Data collector 102 can collect data from sensors 140. Data storage 106 can store the collected data, such as in a database, hard disk drive (HDD), network location, memory location, etc. Region identifier 108 can identify regions within the collected data. One or more models 110 can provide information that can be used to appropriately compress data, such as information for identifying regions and which compression method to use for each region. Expert system 112 can provide a preliminary diagnosis, such as by analyzing the collected data.

Figure 2:
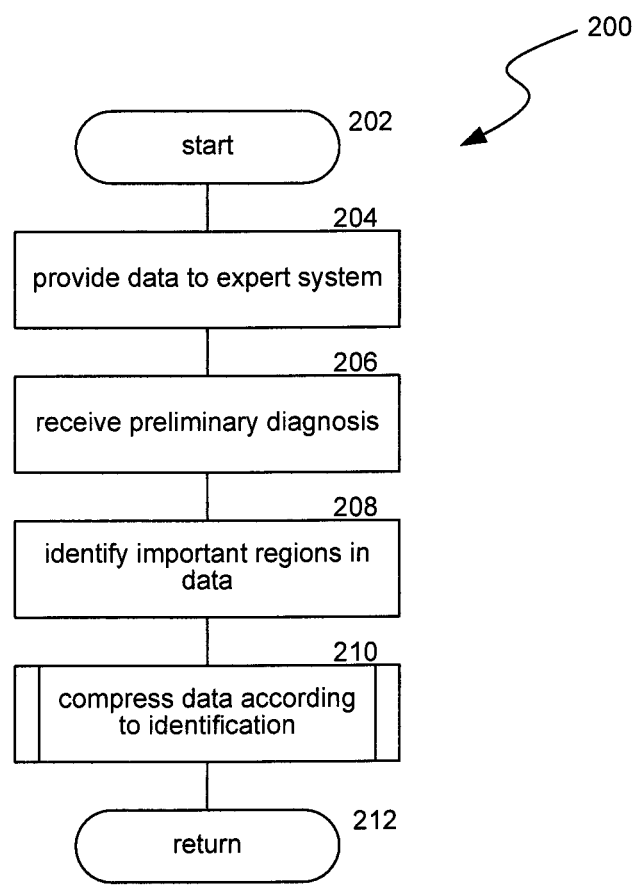
FIG. 2 is a flow diagram illustrating a routine to apply semantic compression in some embodiments.

FIG. 2 is a flow diagram illustrating a routine 200 to apply semantic compression in some embodiments. Routine 200 begins at block 202. At block 204, the routine provides data to an expert system. The data is associated with a patient and can be, e.g., data collected from sensors. As an example, the routine provides data previously received and stored to the expert system. At block 206, the routine receives a preliminary diagnosis from the expert system. In some embodiments, routine 200 does not employ an expert system at block 204 and instead receives the preliminary diagnosis at block 206 from, for example, a user. At block 208, the routine identifies important regions in the data. As an example, the routine may employ region identifier 108 and model 110, which are illustrated above in relation to FIG. 1, to identify the regions. At block 210, the routine invokes a subroutine to compress the received and stored data according to the identification of the regions. This subroutine is described below in relation to FIG. 3. The routine returns at block 212.

Those skilled in the art will appreciate that the steps shown in FIG. 2 and in each of the flow diagrams discussed herein may be altered in a variety of ways. For example, the order of the logic may be rearranged; substeps may be performed in parallel; shown logic may be omitted, or other logic may be included; etc. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 3:
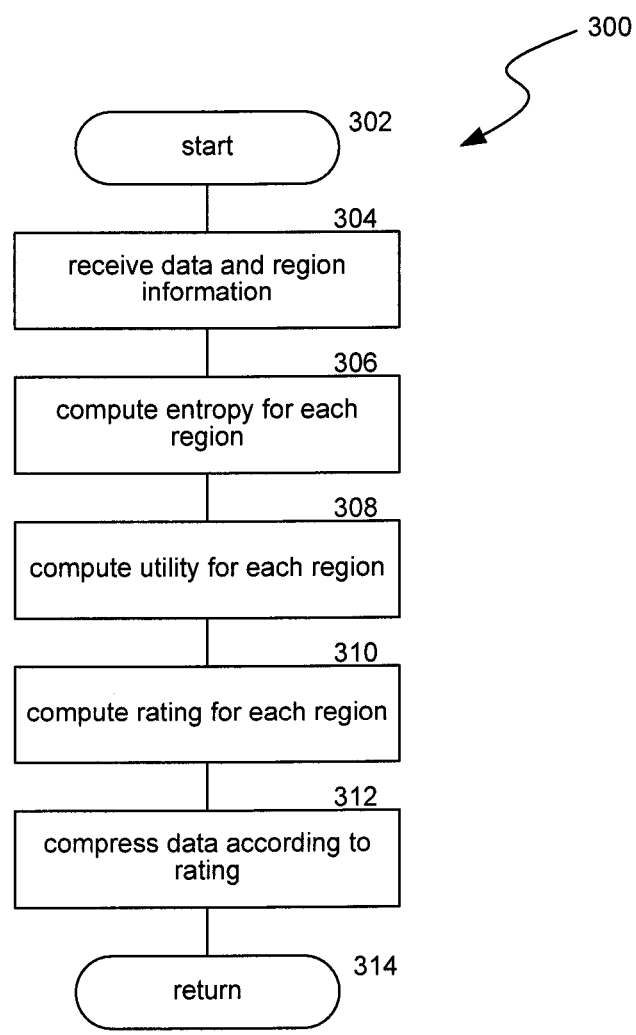
FIG. 3 is a flow diagram illustrating a routine to compress data according to utility values applied to regions of data in some embodiments.

FIG. 3 is a flow diagram illustrating a routine 300 to compress data according to utility values applied to regions of data in some embodiments. Routine 300 begins at block 302. At block 304, the routine receives previously stored data and region information. In various embodiments, the routine may execute in real time, in which case it may receive data collected in real time. At block 306, the routine computes an entropy for each region. In some embodiments, the entropy may be computed using formula $$H(X) = -\text{sum}(p(x) \log (p(x)))$$

where H(x) is the entropy, p(x) is the probability mass function for the data over all values of x, and sum(Y) is the sum of all values in Y. At block 308, the routine computes the utility for each region. In various embodiments, the utility may be specified by a model for the preliminary diagnosis. The utility for any given region X may be represented by the formula:

$$U(X)$$

At block 310, the routine computes a rating for each region. In some embodiments, the rating may be a function of the utility and the entropy for a region and may be computed using formula $$R(X) = U(X)/H(X)$$

At block 312, the routine compresses the data according to the rating. As an example, the routine may apply a lossless compression method to a region that has a high rating and a lossy compression method to a region that has a lower rating. In some embodiments, the routine may apply lossless compression to data contained in regions with ratings higher than a specified threshold. At block 314, the routine returns.

Figure 4:
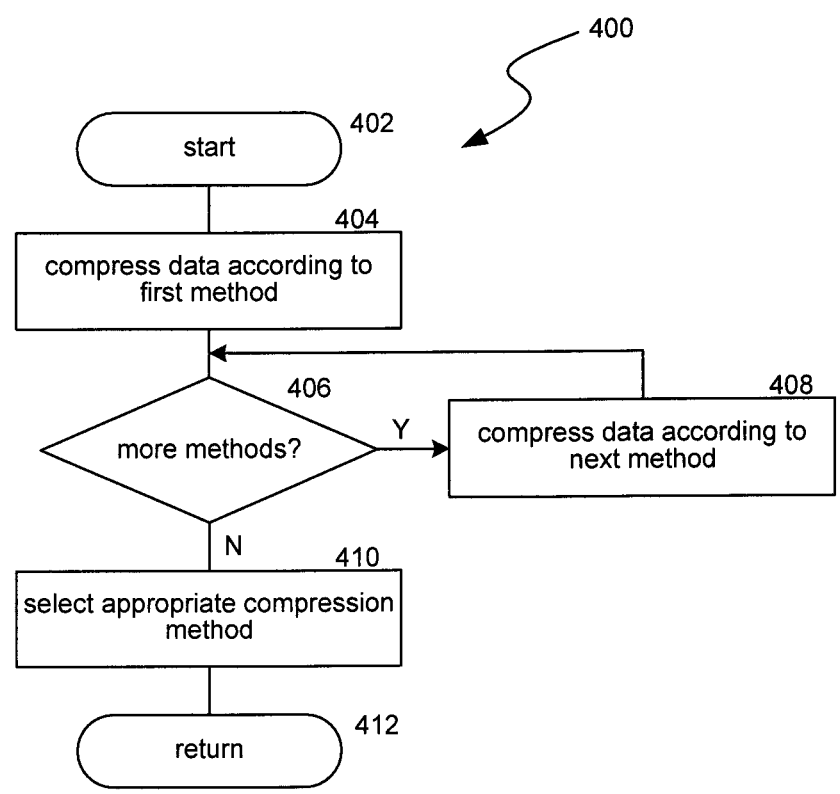
FIG. 4 is a flow diagram illustrating a routine to select an appropriate compression method in some embodiments.

FIG. 4 is a flow diagram illustrating a routine 400 to select an appropriate compression method in some embodiments. Routine 400 begins at block 402. At block 404, the routine compresses data according to a first compression method. At decision block 406, the routine determines whether there are more compression methods that can be attempted. If there are more compression methods that can be attempted, the routine continues at block 408. Otherwise, the routine continues at block 410. At block 408, the routine selects a next compression method and compresses the data according to the selected compression method. The routine then continues at decision block 406. At block 410, the routine selects an appropriate compression method. As an example, the routine may select a compression method that achieves a specified objective, such as low error and high compression. The routine then returns at block 412.

Figure 5:
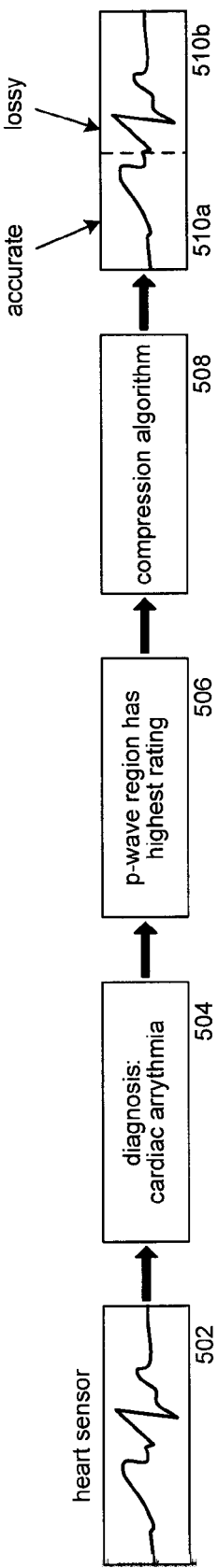
FIG. 5 is a flow diagram illustrating application of the semantic compression technology to the field of medicine in some embodiments.

FIG. 5 is a flow diagram illustrating application of the semantic compression technology to the field of medicine in some embodiments. At block 502, the semantic compression technology receives EKG signal data 502 from one or more heart sensors. At block 504, the semantic compression technology receives a preliminary diagnosis of cardiac arrhythmia. At block 506, the routine determines from a model that, based on the preliminary diagnosis of cardiac arrhythmia, a P-wave region of the received data has a higher rating than other regions of the received data. At block 508, the routine selects a compression algorithm for the P-wave region that provides lossless compression 510a and a different compression algorithm for the other regions of the received data that provides lossy compression 510b.

Figure 6:
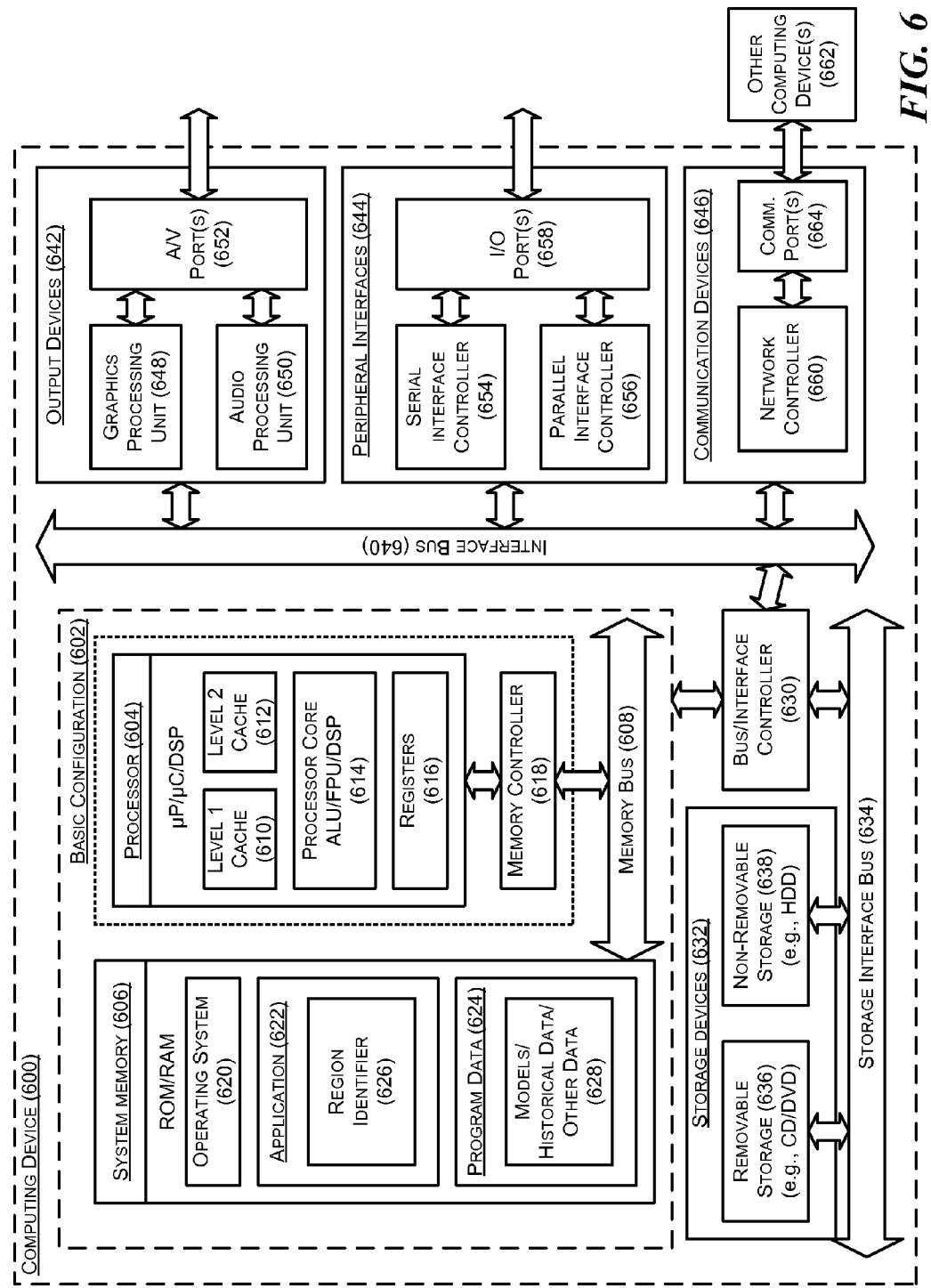
FIG. 6 is a block diagram illustrating an example of a computing device that can be arranged as a suitable computing system for use with the feedback technology in accordance with the present disclosure.

FIG. 6 is a block diagram illustrating an example of a computing device that can be arranged as a suitable computing system for use with the semantic compression technology in accordance with the present disclosure. In a very basic configuration 602, computing device 600 typically includes one or more processors 604 and a system memory 606. A memory bus 608 may be used for communicating between processor 604 and system memory 606.

Depending on the desired configuration, processor 604 may be of any type including but not limited to a microprocessor (µP), a microcontroller (µC), a digital signal processor (DSP), or any combination thereof. Processor 604 may include one or more levels of caching, such as a level one cache 610 and a level two cache 612, a processor core 614, and registers 616. An example processor core 614 may include an arithmetic logic unit (ALU), a floating point unit (FPU), a digital signal processing core (DSP core), or any combination thereof. An example memory controller 618 may also be used with processor 604, or in some implementations, memory controller 618 may be an internal part of processor 604.

Depending on the desired configuration, system memory 606 may be of any type including but not limited to volatile memory (such as RAM), non-volatile memory (such as ROM, flash memory, etc.) or any combination thereof. System memory 606 may include an operating system 620, one or more applications 622, and program data 624. Application 622 may include one or more components (e.g., a region identifier 626) that are arranged to generate and maintain models as described herein. The software components may employ hardware devices, such as sensors. Program data 624 may include models/historical data/other data 628 that may be useful for generating and maintaining models. In some embodiments, application 622 may be arranged to operate with program data 624 on operating system 620. This described basic configuration 602 is illustrated in FIG. 6 by those components within the inner dashed line.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 600 may also be implemented as a personal computer including both laptop computer and non-laptop computer configurations.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, systems, or other specific examples or embodiments disclosed herein. It is also to be understood that the terminology used herein is for the purpose of describing particular embodiments only, and is not intended to be limiting.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

Figure 7:
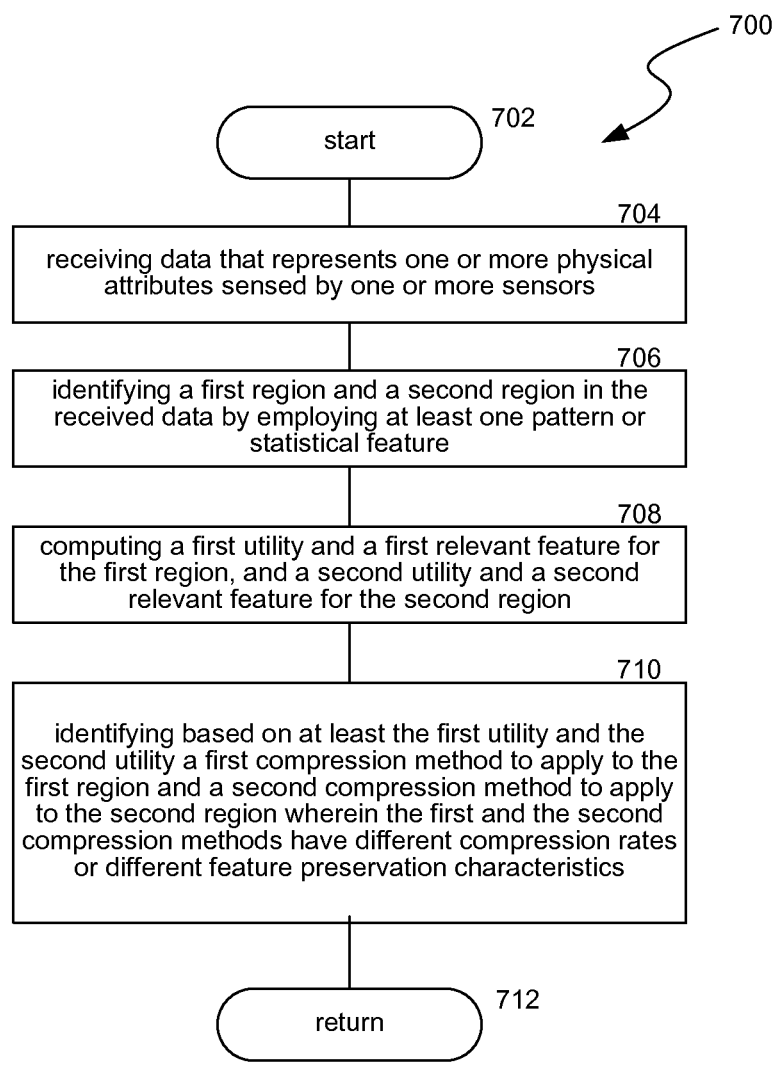
FIG. 7 is a flow diagram illustrating a semantic compression method invoked by the technology in some embodiments.

FIG. 7 is a flow diagram illustrating a semantic compression method invoked by the technology in some embodiments. The method begins at block 702. At lock 704, the method receives data that represents one or more physical attributes sensed by one or more sensors. At block 706, the method identifies a first region and a second region in the received data, e.g., by employing at least one pattern or statistical feature. At block 708, the method computes a first utility and a first relevant feature for the first region, and a second utility and a second relevant feature for the second region. At block 710, the method identifies based on at least the first utility and the second utility a first compression method to apply to the first region and a second compression method to apply to the second region wherein the first and the second compression methods have different compression rates or different feature preservation characteristics. At block 712, the method returns.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive (HDD), a compact disk (CD), a digital versatile disk (DVD), a digital tape, a computer memory, etc.; and a transmission type medium such as a digital and/or an analog communication medium (e.g., a fiber optic cable, a waveguide, a wired communication link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

We claim:

1. A method performed by a computing device to compress medical data, the method comprising:
receiving, by the computing device, the medical data that represents one or more physical attributes;
identifying, by the computing device, a first region and a second region in the received medical data by:
characterizing a utility of different signal segments by analyzing one or more sets of diagnosis results for a first diagnosis, the utility corresponding to how important each of the signal segments is to the first diagnosis compared to other signal segments,
identifying a unique combination of features in each of the signal segments, and
deriving one or more algorithms for automatic feature identification using at least one of a pattern matching technique or a statistical technique to segment the received medical data into the first region and the second region such that each of the first region and the second region has a same utility value;
computing, by the computing device, a first entropy for the first region and a second entropy for the second region;
computing, by the computing device, a first utility value and a first feature for the first region, and a second utility value and a second feature for the second region, wherein the first utility value is representative of a relative measure of how important the first region is to the first diagnosis compared to the second region, and wherein the second utility value is representative of a relative measure of how important the second region is to the first diagnosis compared to the first region;
computing, by the computing device, a first rating for the first region and a second rating for the second region, wherein the first rating is a function of the first utility value and the first entropy, and the second rating is a function of the second utility value and the second entropy, and wherein the first rating is proportional to the first utility value and inversely proportional to the first entropy, and the second rating is proportional to the second utility value and inversely proportional to the second entropy;
determining, by the computing device, whether the first rating is greater than the second rating;
in response to determining that the first rating is greater than the second rating:
compressing, by the computing device, the first region of the received medical data using a first compression technique, and
compressing, by the computing device, the second region of the received medical data using a second compression technique,
wherein the second compression technique is more lossy than the first compression technique; and
in response to determining that the first rating is less than or equal to the second rating:
compressing, by the computing device, the first region of the received medical data using the second compression technique, and
compressing, by the computing device, the second region of the received medical data using the first compression technique,
wherein the first region and the second region are respectively compressed in accordance with a compression technique selected based on at least a measure of how important that region is to the first diagnosis and respective entropy for the first region and the second region.

2. The method of claim 1, wherein at least one of the analyzing or the deriving comprises employing one or more dynamic programming pattern matching or statistical techniques.

3. The method of claim 1 wherein the identifying the unique combination of features in each of the signal segments comprises employing a statistical technique.

4. The method of claim 1, wherein the deriving comprises employing a combinatorial or numerical pattern matching technique.

5. The method of claim 1, further comprising repeating the characterizing, identifying, and deriving until a resulting model does not pass a learn and test criterion.

6. The method of claim 1, further comprising repeating the characterizing, identifying, and deriving until a resulting model does not pass a resubstitution test.

7. The method of claim 6, wherein the resubstitution test includes a jackknife resubstitution test.

8. The method of claim 1, wherein at least one of the first and the second compression techniques is selected by comparing at least one of different compression rates or different feature preservation characteristics after applying the first and second compression techniques to two or more sets of data.

9. The method of claim 8, further comprising building a statistical model based on the application of the first and second compression techniques to the two or more sets of data and employing the statistical model to select the first and second compression techniques.

10. The method of claim 1, wherein the medical data is preprocessed using one or more signal processing techniques.

11. The method of claim 10, wherein the one or more signal processing techniques include at least one of a linear transformation or a difference-based technique.

12. The method of claim 1, wherein the first compression technique is lossless.

13. The method of claim 1, further comprising iteratively identifying additional regions in the received medical data until a stopping criterion is satisfied.

14. The method of claim 13, wherein the stopping criterion includes at least one of a running time of overall procedure or a lack of compression rate improvement.

15. The method of claim 1, wherein the compressing using the first and second compression techniques, respectively for the first region and the second region, comprises applying a dynamic programming technique.

16. The method of claim 1, wherein the compressing using the first compression technique or the second compression technique for the first region is controlled by specifying the first utility value using a joint utility function based on a first utility function and a second utility function, and wherein the joint utility function indicates a relative utility value of the first region if the second utility value of the second region has a particular value.

17. The method of claim 16, wherein the first region relates to a first signal from a first sensor and the second region relates to a second signal from a second sensor.

18. The method of claim 16, wherein each of the first utility function, the second utility function, and the joint utility function is defined using probability density functions.

19. The method of claim 18, further comprising:
combining the first utility function and the second utility function using maximum likelihood expectation (MLE), minimal mean-square expected error (MSEE), or multiple explanation variable statistical models.

20. The method of claim 1, further comprising receiving an iteratively updated patient diagnosis, wherein the first utility value is computed based on a previous patient diagnosis and the second utility value is computed based on a current patient diagnosis.

21. The method of claim 20, further comprising receiving external data and modifying the iteratively updated patient diagnosis based on the external data.

22. The method of claim 21, wherein the external data includes at least one of a geolocation, physical time, or a recent activity of a patient.

23. The method of claim 21, wherein the external data includes a statistical or a numerical quantification of a current or recent epidemic.

24. A non-transitory computer-readable storage medium that stores computer-executable instructions that, in response to execution, cause a computing system to perform a method to compress medical data, the method comprising:
    identifying a first region and a second region in the medical data, which represents one or more physical attributes, by:
        characterizing a utility of different signal segments by analyzing one or more sets of diagnosis results for a first diagnosis, the utility corresponding to how important each of the signal segments is to the first diagnosis compared to other signal segments,
        identifying a unique combination of features in each of the signal segments, and
        deriving one or more algorithms for automatic feature identification using at least one of a pattern matching technique or a statistical technique to segment the medical data into the first region and the second region such that each of the first region and the second region has a same utility value;
    computing a first entropy for the first region and a second entropy for the second region;
    computing a first utility value and a first feature for the first region, and a second utility value and a second feature for the second region, wherein the first utility value is representative of a relative measure of how important the first region is to the first diagnosis compared to the second region, and wherein the second utility value is representative of a relative measure of how important the second region is to the first diagnosis compared to the first region;
    computing a first rating for the first region and a second rating for the second region,
        wherein the first rating is a function of the first utility value and the first entropy, and the second rating is a function of the second utility value and the second entropy,
        the first rating being determined by an equation:

$$R_1(X)=U_1(X)/H_1(X)$$

wherein $R_1(X)$ is the first rating, $U_1(X)$ is the first utility value, and $H_1(X)$ is the first entropy, and the second rating being determined by an equation:

$$R_2(X)=U_2(X)/H_2(X)$$

wherein $R_2(X)$ is the second rating, $U_2(X)$ is the second utility value, and $H_2(X)$ is the second entropy; and
    determining whether the first rating is greater than the second rating;
    in response to determining that the first rating is greater than the second rating:
        compressing the first region of the medical data using a first compression technique, and
        compressing the second region of the medical data using a second compression technique,
            wherein the second compression technique is more lossy than the first compression technique; and
    in response to determining that the first rating is less than or equal to the second rating:
        compressing the first region of the medical data using the second compression technique, and
        compressing the second region of the medical data using the first compression technique,
            wherein the first region and the second region are respectively compressed in accordance with a compression technique selected based on at least a measure of how important that region is to the first diagnosis and respective entropy for the first region and the second region.

25. A system to compress medical data, the system comprising:
    a component configured to receive the medical data that represents one or more physical attributes from a plurality of sensors;
    a component configured to identify a first region and a second region in the received medical data by:
        characterization of a utility of different signal segments by analysis of one or more sets of diagnosis results for a first diagnosis, the utility corresponding to how important each of the signal segments is to the first diagnosis compared to other signal segments,
        identification of a unique combination of features in each of the signal segments, and
        derivation of one or more algorithms for automatic feature identification using at least one of a pattern matching technique or a statistical technique to segment the received medical data into the first region and the second region such that each of the first region and the second region has a same utility value;
    a component configured to compute:
        a first entropy for the first region and a second entropy for the second region,
        a first utility value and a first feature for the first region, and a second utility value and a second feature for the second region, wherein the first utility value is representative of a relative measure of how important the first region is to the first diagnosis compared to the second region, and wherein the second utility value is representative of a relative measure of how important the second region is to the first diagnosis compared to the first region, and
        a first rating for the first region and a second rating for the second region,
            wherein the first rating is a function of the first utility value and the first entropy, and the second rating is a function of the second utility value and the second entropy, and
            wherein the first rating is proportional to the first utility value and inversely proportional to the first entropy, and the second rating is proportional to the second utility value and inversely proportional to the second entropy;
    a component configured to:
        compare different compression rates or different feature preservation characteristics for at least a first compression technique and a second compression technique after application of the first compression technique and the second compression technique to two or more sets of the received medical data; and
determine whether there is another compression technique to utilize;
a component configured to:
in response to a determination that the second compression technique is more lossy than the first compression technique and there is no other compression technique to utilize:
determine whether the first rating is greater than the second rating; and
a component configured to:
in response to a determination that the first rating is greater than the second rating:
compress the first region of the received medical data using the first compression technique; and
compress the second region of the received medical data using the second compression technique; and
in response to a determination that the first rating is less than or equal to the second rating:
compress the first region of the medical received data using the second compression technique; and
compress the second region of the received medical data using the first compression technique,
wherein the first region and the second region are respectively compressed in accordance with a compression technique selected based on at least a measure of how important that region is to the first diagnosis and respective entropy for the first region and the second region.

26. The non-transitory computer-readable storage medium of claim 24, wherein the first compression technique includes a lossless compression technique and the second compression technique includes a lossy compression technique, wherein, in response to the determination that the first rating is greater than the second rating, the lossless compression technique is selected to be used to compress the first region and the lossy compression technique is selected to be used to compress the second region, and wherein, in response to the determination that the second rating is greater than the first rating, the lossy compression technique is selected to be used to compress the first region and the lossless compression technique is selected to be used to compress the second region.

* * * * *

UNITED STATES PATENT AND TRADEMARK OFFICE
CERTIFICATE OF CORRECTION

PATENT NO. : 9,858,393 B2  
APPLICATION NO. : 12/997862  
DATED : January 2, 2018  
INVENTOR(S) : Beckmann et al.

It is certified that error appears in the above-identified patent and that said Letters Patent is hereby corrected as shown below:

In Column 20, Line 7, in Claim 3, delete "claim 1 wherein" and insert -- claim 1, wherein --, therefor.

In Column 23, Line 23, in Claim 25, delete "medical received data" and insert -- received medical data --, therefor.

Signed and Sealed this  
Twentieth Day of March, 2018

Andrei Iancu  
*Director of the United States Patent and Trademark Office*